United States Patent
Li et al.

(10) Patent No.: US 11,422,106 B2
(45) Date of Patent: Aug. 23, 2022

(54) USING 4-ACETOXYPHENOL AS A SUBSTRATE FOR MODULAR HYDROLASE BIOSENSORS

(71) Applicant: United States Government, as represented by the Administrator of the U.S. EPA, Washington, DC (US)

(72) Inventors: Tao Li, Loveland, OH (US); Endalkachew Sahle-Demessie, Mason, OH (US)

(73) Assignee: United States Government, as represented by the Administrator of the U.S. EPA, Washington, DC (US)

( * ) Notice: Subject to any disclaimer, the term of this patent is extended or adjusted under 35 U.S.C. 154(b) by 394 days.

(21) Appl. No.: 16/793,455

(22) Filed: Feb. 18, 2020

(65) Prior Publication Data

US 2020/0264124 A1 Aug. 20, 2020

Related U.S. Application Data

(60) Provisional application No. 62/918,897, filed on Feb. 19, 2019.

(51) Int. Cl.
*G01N 27/327* (2006.01)
*G01N 33/18* (2006.01)
*C12Q 1/46* (2006.01)

(52) U.S. Cl.
CPC .......... *G01N 27/3271* (2013.01); *C12Q 1/46* (2013.01); *G01N 33/18* (2013.01)

(58) Field of Classification Search
CPC ...... G01N 27/3271; G01N 33/18; C12Q 1/46; C12Q 1/005; C12Q 1/34; C12Q 1/26; C12Q 1/28; C12Q 1/42; C12Q 1/44; Y10S 435/963; Y10S 435/97; C12Y 301/01007
See application file for complete search history.

(56) References Cited

U.S. PATENT DOCUMENTS

| 6,406,876 B1 | 6/2002 | Gordon et al. |
| 6,730,212 B1 | 5/2004 | Yamagishi et al. |
| 2005/0244811 A1* | 11/2005 | Soundarrajan ......... B82Y 30/00 435/287.1 |

OTHER PUBLICATIONS

Determination of organophosphorus and carbamic pesticides with an acetylcholinesterase amperometric biosensor using 4-aminophenyl acetate as substrate; C. La Rosa et al; Analytics Chimica Acta 295 (1994) 273-282; 10 pages.
4-Acetoxyphenol as a substrate for acetylcholinesterase-based sensor and its application for As(III) determination; Tao Li et al; American Chem. Society; vol. 256; Aug. 2018; 23 pages.
A disposable acetylcholine esterase sensor for As(III) determination in groundwater matrix based on 4-acetoxyphenol hydrolysis; Tao Li et al; Analytical Methods 2019; Issue 40; Sep. 26, 2019; 27 pages.
(Continued)

*Primary Examiner* — Jennifer Wecker
*Assistant Examiner* — Alea N. Martin
(74) *Attorney, Agent, or Firm* — Mark E. Bandy; Rankin Hill & Clark, LLP

(57) ABSTRACT

Biosensors utilizing 4-acetoxyphenol are described. The biosensors typically include 4-acetoxyphenol in a substrate and utilize one or more enzymes to detect the presence of pollutant agents. Also described are related methods using the biosensors to detect the presence of pollutant agents in water such as As(III).

17 Claims, 10 Drawing Sheets

(56) References Cited

OTHER PUBLICATIONS

Managing Groundwater contamination by Arsenic and the Need for Field Analysis (Tao Li's Part); Tao Li; Book: Evaluating water quality to prevent future disasters; Elsevier publishing; Jul. 2018; 20 pages.
Screen printed electrodes; www.pineresearch.com (2 pages).

* cited by examiner

USING 4-ACETOXYPHENOL AS A SUBSTRATE FOR MODULAR HYDROLASE BIOSENSORS

CROSS REFERENCES TO RELATED APPLICATIONS

This application claims priority from U.S. provisional application Ser. No. 62/918,897 filed on Feb. 19, 2019.

FIELD

The present subject matter relates to biosensors and related methods for detecting and measuring pollutants.

BACKGROUND

Arsenic contamination of groundwater has been found in many places under a wide range of hydrogeochemical conditions. The arsenic in groundwater is predominantly inorganic, with concentrations varying from <0.5 to 5,000 $\mu g\ L^{-1}$. Since the 1930's, many arsenic poisoning incidents have been reported. Most incidents were caused by ingestion of groundwater polluted by geogenic or anthropogenic arsenic. Systematic study has demonstrated that arsenic is a carcinogen and a general toxin. Long-term ingestion of arsenic causes not only skin, bladder, or lung cancer; but also damage to the neural, cardiovascular, and reproductive systems. For vulnerable people, the harmful level can be as low as <1 $\mu g L^{-1}$.

The primary source of groundwater arsenic pollution can be geogenic or anthropogenic. In anthropogenic pollution, arsenic is released from sites with a history of mining or smelting, coal burning, manufacture or application of arsenic agrochemicals, and wood preservation with chromated copper arsenate. Once arsenic is released from the primary sources into groundwater, it undergoes redistribution through redox reactions, sequestration by forming minerals in sediment, and desorption or dissolution from the sediments.

To manage anthropogenic pollution, the primary source needs to be characterized, contained, and treated. Runoff of arsenic from primary source(s) causes acute impact on local lives, diffuse pollution downstream, and pollutant infiltration of groundwater. Examples include fish kills by unmanaged acid mine drainage, expansive arsenic pollution resulting from mine flood or uncontrolled discharge from arsenic chemical plant(s). For mine waste management, the contamination at the site needs to be characterized in terms of mineral source, contaminant abundance in the minerals, reactivity of the minerals, and main flow path of the contaminated water. Anthropogenic site remediation can be time consuming and expensive. At Vinland Superfund site, the cleanup involved excavation and flushing of 682,558 tons of contaminated soil, pumping and treating two million gallons of groundwater per day. As of 2018, the project has cost $219.4 million since the start of cleanup in 1992.

Arsenic contamination was a concern in one third of the superfund sites in the US. A special type of pollution is caused by leachate from landfills, as it can mobilize arsenic in sediments by reductive dissolution. The pollution needs to be managed and treated to prevent diffusion to surface water. This effort entails monitoring and characterization of the flow path, plume distribution, and composition of groundwater.

Arsenic speciation is essential for the understanding of pollution source and pollutant transportation. Inorganic arsenic exists as As(III) and As(V) in $As-O_2-H_2O$ system, with distribution governed by pH and redox potential. As(III) is the predominant species under reductive and acid-to-neutral condition. In natural water, arsenic mobilization and re-distribution depends on the interconversion of As(III) and As(V). This interconversion is complex as it is directly coupled to the redox reactions involving iron, sulfur, and manganese at specific location(s).

As(III) was suggested as the dominant species in groundwater pollution caused by landfill leachate, but the instability of As(III) in samples casted doubts on the accuracy of earlier results in lab analysis. This is a significant concern because As(III) is highly different from As(V) in toxicity, bioavailability, mobility, and remediation need. Inorganic arsenic specification in the lab usually involves a chromatographic separation and a spectrometric detection. Although separation-spectrometry methods are highly sensitive and accurate, environmental sampling and sample management have been difficult. Samples from the field generally need to be cleaned, acidified, and stored under controlled condition, mainly to prevent As(III) oxidation. However, general treatment is often inadequate because arsenic can be precipitated by adsorption to iron oxide minerals when a sample is exposed to oxygen or formation of orpiment ($As_2S_3$) when acidified. Preservation methods need to be systematically developed for specific matrix to allow adequate time for lab analysis.

The sampling issues are commonly mitigated with in-field separation. Different species of arsenic are separated with solid phase extractions and sent for lab analysis. In this procedure, water matrix may have strong impact on extraction capacity and the analysis throughput is still limited by sample management.

Electroanalysis based on different types of stripping voltammetry have been used in field speciation. Although these methods are highly sensitive, they are still in development for routine environmental monitoring. Notable issues to be addressed include: robustness of electrodes, passivation of electrodes, interference caused by common elements such as Cu(II), requirement for HCl (2 M) as electrolyte solution, and cost of instrumentation, etc.

Many biomolecules can selectively bind to arsenic with different mechanisms for As(III) and As(V), therefore they may be used as bioreceptors for speciation. These biomolecules include DNA fragments, aptamers, and enzymes or proteins. The specific interactions have been employed to develop many optical and electrochemical sensors. However, most of the reported biosensors are not ready for field use because they do not meet important practical qualifications. The fabrication needs to be simple yet tunable for mass production. The resulting sensors must be stable in storage, deployment, and operation. Finally, potential biosensors should maintain their selectivity and sensitivity in realistic water matrices.

SUMMARY

The difficulties and drawbacks associated with previous approaches are addressed in the present subject matter as follows.

In one aspect, the present subject matter provides a biosensor for analyzing a sample for pollutant agents in water. The biosensor comprises a substrate, an electrode, and at least one enzyme immobilized on the electrode. The substrate includes 4-acetoxyphenol.

In another aspect, the present subject matter provides a biosensor for analyzing a sample. The biosensor comprises a substrate including 4-acetoxyphenol. The substrate defines a first face and a second face. The biosensor also comprises a working electrode disposed on the first face of the substrate. The biosensor additionally comprises a region including at least one enzyme disposed on the working electrode.

In yet another aspect, the present subject matter provides a method for detecting presence of a pollutant agent. The method comprises providing a biosensor including a substrate having 4-acetoxyphenol, a working electrode disposed on the substrate, and a region including at least one enzyme disposed on the working electrode. The method also comprises exposing the biosensor to an aqueous sample. And, the method comprises monitoring electrical activity at the working electrode.

As will be realized, the subject matter described herein is capable of other and different embodiments and its several details are capable of modifications in various respects, all without departing from the claimed subject matter. Accordingly, the drawings and description are to be regarded as illustrative and not restrictive.

DETAILED DESCRIPTION OF THE EMBODIMENTS

Figure 1:
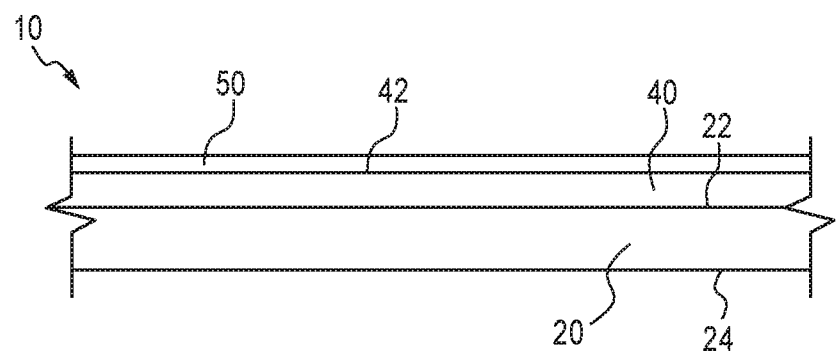
FIG. 1 is a schematic cross sectional view of an embodiment of a biosensor in accordance with the present subject matter.

Generally, the present subject matter provides various biosensors which utilize reaction(s) between 4-acetoxyphenol and one or more enzymes, to produce hydroquinone and electrical current which in turn is used to indicate the presence and/or concentration of certain agents such as pollutant agents in an aqueous environment. The presence of the pollutant agent(s) changes the activity of the enzyme which is reported by a transduction mechanism involving hydrolysis of 4-acetoxyphenol and oxidation of hydroquinone. The present subject matter also provides various methods of use of the biosensors such as for detecting and monitoring the presence of pollutant agents.

To minimize developmental risk, an amperometric assay was selected using acetylcholinesterase (AchE) as the bioreceptor. AchE is known to be inhibited by As(III). The enzyme is not only extremely efficient, but also highly stable in solution. For field use, electrochemical transduction is preferred because it is highly sensitive and can be miniaturized. Carbon screen-printed electrodes (SPE) were selected as the base because of their low cost, flexibility, suitability for mass production, and robustness when used in different aqueous matrices. In addition, disposal of AchE sensors has less regulatory restrictions because the analysis does not involve hazardous chemicals or genetically modified organisms.

In accordance with the present subject matter, 4-acetoxyphenol was selected for use as a biosensor substrate based on the assumptions that it would be efficiently hydrolyzed by AchE but not oxidized at the working potential of the hydrolysis product hydroquinone, see Reactions 1 and 2. It is believed that the selectivity of Reaction 2 on a carbon electrode would not require a redox mediator, thereby simplifying sensor fabrication. Reactions 1 and 2 show amperometric assay of AchE activity with 4-hydroxyphenol as the substrate. The signal (electric current) by amperometric assay depends on the reaction rate of the two-reaction sequence, involving hydrolysis by the immobilized AchE and anodic oxidation. By design, the rate limiting step of the sequence is Reaction 1. Therefore, the current in amperometric assay solely depends on the activity of AchE.

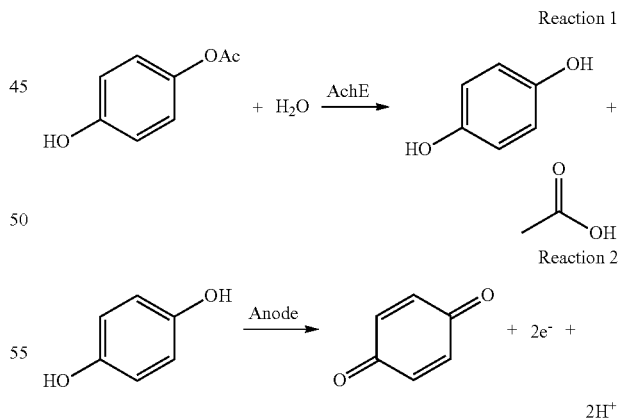

The present subject matter biosensors are not limited to the use of 4-acetoxyphenol in the biosensor substrate. For example, the biosensor could include, in addition to 4-acetoxyphenol, monoesters of benzene diols including hydroquinone (1,4-benzene diol), resorcinol (1,3-benzene diol), and catechol (1,2-benzene diol).

The acyl group can also be varied, such as acetyl, propionyl, butyryl etc.

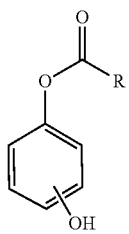

Formula I

Thus, the biosensors of the present subject matter can additionally include in the biosensor substrate, one or more of a monoester of hydroquinone, a monoester of resorcinol, a monoester of catechol, and combinations thereof. The biosensors can include variations of these in which the acyl group is varied, as shown in Formula I in which R is an alkyl group having a number of carbon atoms ranging from 1 to 5 or more, and particularly from 1 to 3.

Although many immobilization methods have been developed, it is difficult to predict their impacts on the kinetics of the immobilized enzymes. Among the options, crosslinking with glutaraldehyde (GA) offers several important advantages. GA is not only highly reactive but also flexible, because it can cross-link lysine residues as oligomers of different lengths. Bovine serum albumin (BSA) is lysine rich therefore is used as the carrier protein. The ratio of BSA with AchE can be adjusted to optimize enzyme performance including activity, sensitivity to As(III), and stability. The cross-linking is straightforward and easy to scale up.

To ensure AchE is acting as the bioreceptor for As(III), the kinetic mechanism of the inhibition has been evaluated with the electrodes and compared with the previous kinetic analysis of the free enzyme. A protocol consistent with the mechanism has been developed for the assay of As(III). The assay has been tested in groundwater matrix and the storage stability of the sensor has been evaluated at ambient temperature for 5 months.

FIG. 1 schematically illustrates an embodiment of a biosensor 10 in accordance with the present subject matter. Specifically, a substrate 20 including 4-acetoxyphenol is provided with a first face 22 and a second face 24. The biosensor 10 further comprises at least one electrode 40 disposed on or in electrical association with the substrate 20. The electrode defines at least one face 42. The biosensor 10 also comprises a layer or region 50 disposed on or in association with the electrode face 42. The layer or region 50 includes at least one enzyme and particularly AchE. It will be understood that typically, the enzyme layer or region is immobilized on region 40, the electrode. This enzyme layer or region is depicted schematically as region 50. As described herein the at least one enzyme typically includes an immobilized hydrolase enzyme. It will be understood that the biosensor may include additional components, layers, electrodes, and/or other features as desired. These and other aspects are described in greater detail herein.

Figure 2:
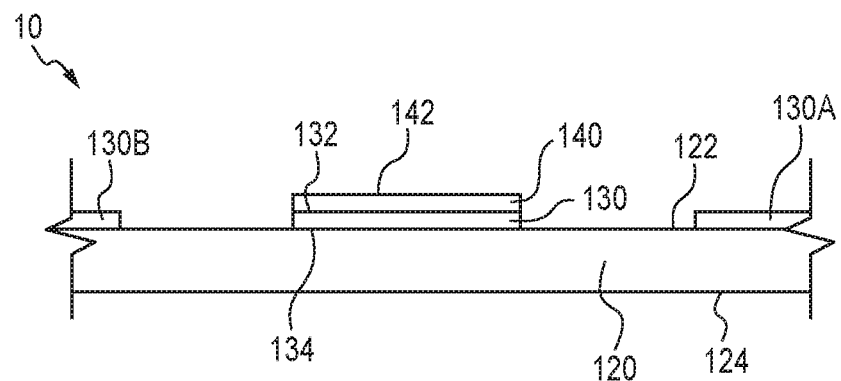
FIG. 2 is a schematic cross sectional view of another embodiment of a biosensor in accordance with the present subject matter.

FIG. 2 illustrates another embodiment of a biosensor 110 in accordance with the present subject matter. Specifically, the biosensor 110 comprises an inert substrate 120 including 4-acetoxyphenol. The substrate 120 defines a first face 122 and a second face 124. The biosensor 110 further comprises a working electrode 130, a reference electrode 130A, and a counter electrode 130B. The working electrode defines a first face 132 and a second face 134. Typically, the working electrode 130, reference electrode 130A, and the counter electrode 130B are disposed on the first face 122 of the substrate 120. The biosensor 110 further comprises a layer or region 140 that includes an immobilized hydrolase enzyme and particularly AchE disposed on the working electrode 130. Typically, the layer or region 140 is disposed on the first face 132 of the working electrode 130. It will be understood that the biosensor may include additional components, layers, electrodes, and/or other features as desired. These and other aspects are described in greater detail herein.

The biosensors of the present subject matter may be implemented and/or provided in a wide array of forms, configurations, and/or structures. Generally, the biosensors are based upon the transduction mechanism as described herein. And so, any sensor configuration that employs anodic oxidation to report hydrolase activity can be used. For example, in certain embodiments, the substrate including 4-acetoxyphenol is not physically integrated in the biosensor. It is in the assay solution. Thus, in these embodiments, the substrate is remote from the remaining components of the biosensor, e.g., the electrode(s) and/or the immobilized enzyme.

As the substrate in activity assay, it diffuses into the enzyme layer, where it is hydrolyzed to give hydroquinone. Since the enzyme is immobilized on the working electrode, the hydroquinone product is immediately oxidized to generate electric current. This configuration basically ensures that hydroquinone is oxidized before it has any chance to diffuse into solution, therefore the enzyme activity is proportional to the current.

Instead of, or in addition to, AchE, the preferred biosensors of the present subject matter can utilize a wide range of enzyme(s). Table 1 set forth below lists a representative list of enzymes suitable for use in the biosensors of the present subject matter. The preferred biosensors can utilize one or more of these enzyme(s) instead of, or in addition to, AchE. It is also contemplated that other enzyme(s) could potentially be used in the biosensors of the present subject matter.

TABLE 1

Suitable Enzymes for Use in the Preferred Biosensors

| Enzyme | Enzyme Activity | Manufacture | Origin | Activity with 4-Acetoxyphenol $\mu mol\ mg^{-1}\ min^{-1}$ |
| --- | --- | --- | --- | --- |
| Lipase AY-S | Lipase | Amano | Can. rugosa | 42.88 |
| Lipase AS | Lipase | Amano | Asp. niger | 4.63 |
| Lipase PS SD | Lipase | Amano | Psu. cepacia | 69.31 |
| Lipase G | Lipase | Amano | Pen. camembertii | 12.61 |
| Lipase AK | Lipase | Amano | Psu. fluorescens | 11.09 |
| Lipase R | Lipase | Amano | Penicillium roqueforti | 0.00 |

TABLE 1-continued

Suitable Enzymes for Use in the Preferred Biosensors

| Enzyme | Enzyme Activity | Manufacture | Origin | Activity with 4-Acetoxyphenol μmol mg$^{-1}$ min$^{-1}$ |
|---|---|---|---|---|
| Lipase DF | Lipase | Amano | *Rhi. oryzae* | 6.24 |
| Lipolase 100 L | Lipase | Novozyme | *Thermomyces lanuginosus* | 1.59 |
| Lipex 100 L | Lipase | Novozyme | | 1.16 |
| NovoCor AD L (Lipase A) | Lipase | Novozyme | *Can. antarctica* | 3.81 |
| Lipozyme CALB L | Lipase | Novozyme | *Can. antarctica* | 2.58 |
| Palatase 20000 L | Lipase | Novozyme | *Rhizomucor miehei* | 3.43 |
| Alcalase 2.5 Type DX | Subtilisin | Novozyme | *Bacillus licheniformis* | 1.93 |
| Savinase 16 L | Subtilisin | Novozyme | *Bacillus* sp. | 18.76 |
| Umamizyme-K | protease | Amano | *Aspergillus oryzae* | 0.64 |
| Peptidase R | protease | Amano | *Rhizopus oryzae* | 8.40 |
| Protease M "Amano" SD | protease | Amano | *Aspergillus oryzae* | 0.16 |
| Protease P "Amano" 6SD | protease | Amano | *Aspergillus melleus* | 0.18 |
| Protease A "Amano" 2SD | protease | Amano | *Aspergillus oryzae* | 0.00 |
| L-Acylase H "Amano" | acylase | Amano | | 0.00 |
| D-amino acylase | acylase | Amano | *E. coli* | 0.00 |

Thus, the biosensors of the present subject matter can utilize at least one enzyme selected from the group consisting of AchE, Lipase AY-S, Lipase AS, Lipase PS SD, Lipase G, Lipase AK, Lipase R, Lipase DF, Lipolase 100 L, Lipex 100 L, NovoCor AD L (Lipase A), Lipozyme CALB L, Palatase 20000 L, Alcalase 2.5 Type DX, Savinase 16 L, Umamizyme-K, Peptidase R, Protease M Amano SD, Protease P Amano 6SD, Protease A Amano2SD, L-Acylase H Amano, D-amino acylase, and combinations thereof.

The present subject matter biosensors can be used to detect and measure the concentration of a wide array of agents. For example, the biosensors can be used to detect essentially any agent that inhibits an enzyme such as a hydrolase if the hydrolase can catalyze the hydrolysis of 4-acetoxyphenol. A non-limiting listing of such agents includes pollutants such as As(III), carbamate, perfluorooctanoic acid (PFAS), mercury, lead, agrochemicals, persistent pollutants, and similar agents.

The present subject matter also provides various methods such as methods of detecting for the presence and/or measuring the concentration(s) of one or more pollutant agents by use of the biosensors. Generally, such methods involve providing a biosensor as described herein, exposing the biosensor to an aqueous sample, and then monitoring or detecting electrical activity or changes in such at one or more electrode(s) of the biosensor.

When the biosensor is exposed to an inhibitor, the enzyme activity decreases. The correlation of activity change to the concentration of inhibitor is employed to determine pollutants, because pollutants can inhibit enzymes specifically. When inhibition is reversible, the inhibition and activity assay are in one step (pollutant and 4-acetoxyphenol in one solution). When inhibition is irreversible, the activity assay and inhibition are in separate steps.

For applications involving detection of As(III), As(III) inhibition is pseudo-irreversible. The inhibition is carried out in the first step. The activity assay is carried out in the next step.

EXAMPLES

Chemicals and Materials

Acetylcholinesterase (E.C. 3.1.1.7) Type VI-S from *Electrophorus electricus* (electric eel) with activity of 217 U mg$^{-1}$ protein, was purchased from Sigma-Aldrich. 4-Acetoxyphenol was purchased from Combi-Blocks (San Diego, Calif., USA). All other chemicals were purchased from Sigma-Aldrich (reagent grade) and used as received.

Carbon Screen Printed Electrodes (SPE), including those with small round working electrodes (2 mm OD, RRPE1001C) and large rectangular working electrodes (4×5 mm, RRPE1002C), were purchased from Pine Research Instrumentation (Durham, N.C., USA).

AchE Immobilization on SPE

A mixture of BSA and AchE (containing 0.50 μg, or 0.11 U of the AchE, 8 μg of BSA in 10 μl of 0.06 M phosphate, pH 7.0) was spread on the working electrode of carbon SPE (RRPE1002C). The proteins were deposited on the electrode surface by air drying, and then crosslinked by adding 10 μl of 0.0021% of glutaraldehyde solution in water. The electrode was air dried at room temperature for 16 h to complete the crosslinking. To hydrate the sensor, it was stored in 0.1 M Tris-HCl, pH 7.0 for >24 h at room temperature before use.

Electrochemical Measurements

Electrochemical evaluations were carried out in the low volume SPE cell (Pine Research Instrumentation, Durham, N.C., USA), and the conditions controlled by a DY2013 Potentiostat with DY2000 software (Digi-Ivy, Inc. Austin, Tex., USA). The working potential was set with the Ag/AgCl electrode on the SPE as the reference. For cyclic voltammetry study, the SPE with a small working electrode (2 mm ID round, RRPE1001C) was used. For chronoamperometry study and AchE electrode preparation, the SPE with a larger working electrode was utilized (4×5 mm rectangular RRPE1002C).

All evaluations were carried out at 22±2° C. The current in amperometric determination was recorded for 150 s. The current typically stabilized in <60 s. The average of the readings between 120 s and 150 s was used as the steady-state current. The collected data was exported to Excel for data presentation and analysis.

Inhibition of Immobilized AchE by Sodium Arsenite

The inhibition of the immobilized AchE by As(III) was investigated for protocol development. An AchE electrode was incubated in a NaAsO$_2$ solution for varying periods of time before removal to determine the residual activity. The inhibition was determined by the decrease of steady state current during amperometric measurement. The concentrations of NaAsO$_2$ were 5, 20 and 100 μM, and the incubation times were varied between 1 min and 60 min. The inhibition data was fit to a reversible pseudo-first order reaction model (Equation 1) using a non-linear least-square method.

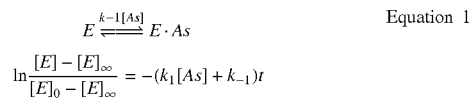

Equation 1

$$\ln\frac{[E] - [E]_\infty}{[E]_0 - [E]_\infty} = -(k_1[As] + k_{-1})t$$

[As(III)] Determination Protocol

The concentration of As$^{3+}$ was determined by its correlation with the degree of inhibition of AchE. The AchE electrode was incubated with arsenite solution in 0.1 M Tris-HCl, pH 8.0 for 1 h at 22±2° C. The activity of the electrode was measured before and after the inhibition with an amperometric method based on the reaction sequence in FIG. 1. The inhibition was calculated by Equation 2, where I is inhibition, $i_0$ is the steady state current in the absence of As$^{3+}$, and $i_i$ is the steady state current of the electrode after inhibition.

$$I = \frac{i_0 - i_i}{i_0}$$

Equation 2

Experimental planning and analysis were carried out with JMP software (SAS Institute, Cary, N.C., USA)

Total Arsenic Determination with ICP-AES

Total arsenic (including As(III) and As(V)) was determined with an iCAP 6500 Inductively Coupled Spectrometer (Thermo Scientific, Waltham, Mass., USA). The detection limit is 5 ppb.

Results and Discussion

Electrochemical Characterization of the Substrate and Product

The electrochemical reactions were first evaluated with 5 mM solutions of 4-acetoxyphenol or hydroquinone (QH$_2$) in 0.1 M phosphate, pH 7.0. Cyclic voltammetry was performed with initial potential at -0.8 V, scan rate at 50 mV s$^{-1}$, and switching potential at 0.8 V.

Figure 3:
FIG. 3 illustrates cyclic voltammograms for hydroquinone with scanning rate from 20-1000 mV/s (5 mM in 0.1M phosphate, pH 7.0, 23° C.).
Figure 3:
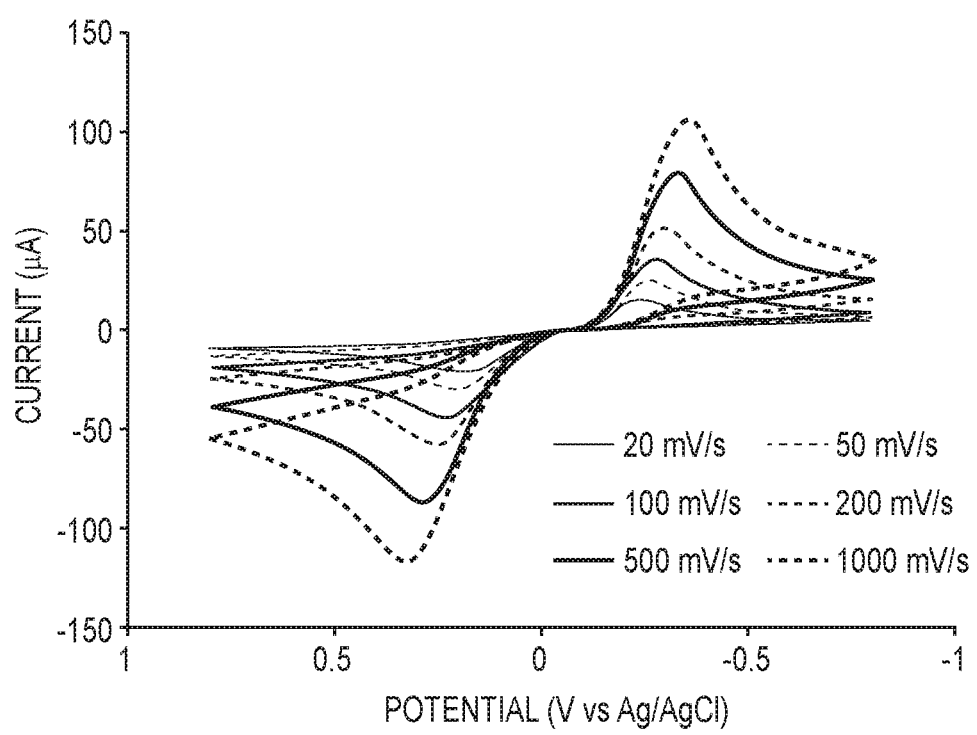

Hydroquinone gave two well defined peaks at 195 and -275 mV in the voltammogram, see FIG. 3. These peaks were reproducible in successive scans with the same electrode. The peak separation at 50 mV s$^{-1}$ scan rate was 470 mV, indicating the interfacial kinetics was slow. Further investigation showed that the peak potential was a function of scanning rate. The peak potential separation increased from 420 to 672 mV as the scan rate increased from 20 to 1000 mV s$^{-1}$. The peak current ratios were in the range between 0.85 and 1.09, see FIG. 3 and Table 2.

TABLE 2

The Impact of Scan Rate on the Voltammograms of Hydroquinone

| Scan Rate (mV s$^{-1}$) | $E_{pa}$ (V) | $i_{pa}$ (μA) | $E_{pc}$ (V) | $i_{pc}$ (μA) | $i_{pa}/i_{pc}$ (μA) | ΔE (V) |
|---|---|---|---|---|---|---|
| 20 | 0.181 | 22.499 | -0.239 | 20.592 | 1.09 | 0.420 |
| 50 | 0.207 | 30.076 | -0.259 | 31.684 | 0.95 | 0.466 |
| 100 | 0.225 | 36.859 | -0.282 | 43.259 | 0.85 | 0.507 |
| 200 | 0.245 | 53.975 | -0.302 | 55.109 | 0.98 | 0.547 |
| 500 | 0.286 | 78.258 | -0.330 | 77.501 | 1.01 | 0.616 |
| 1000 | 0.319 | 103.430 | -0.353 | 104.971 | 0.99 | 0.672 |

Figure 4:
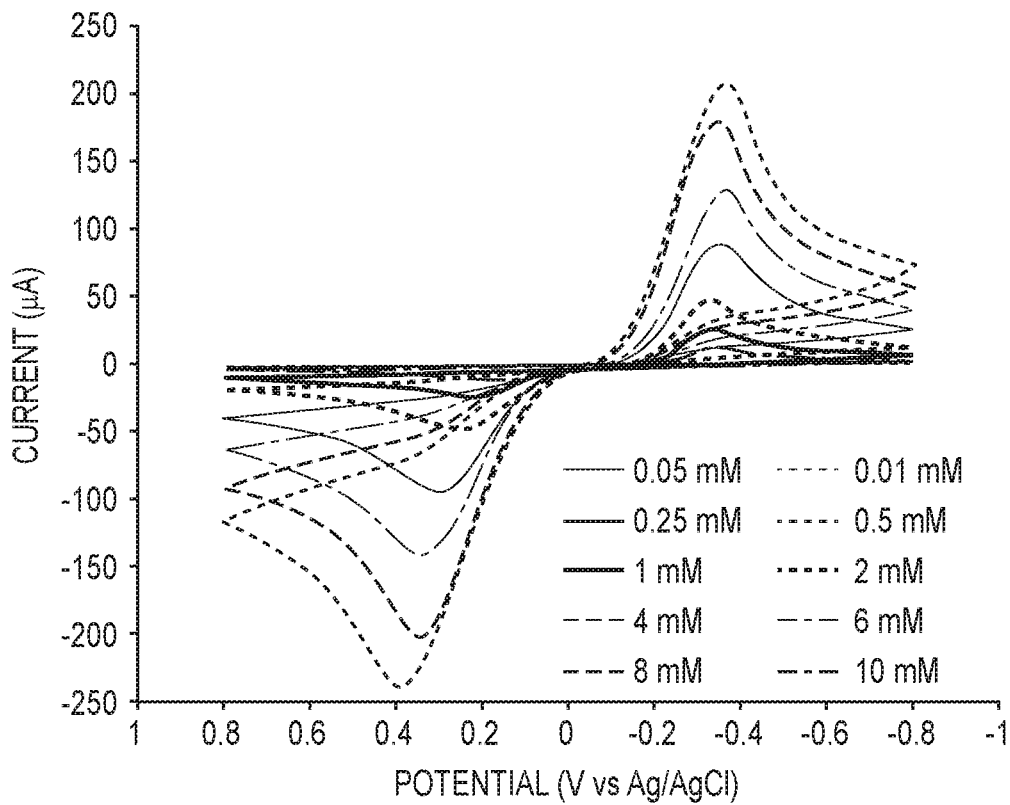
FIG. 4 illustrates cyclic voltammograms for hydroquinone at concentrations from 0.05-10 mM (1000 mV/s in 0.1M phosphate, pH 7.0).
Figure 5:
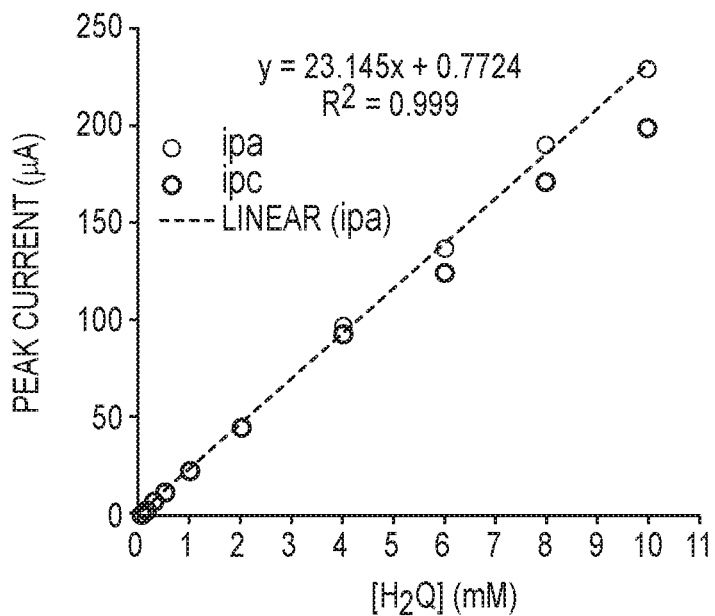
FIG. 5 is a standard curve of peak current of hydroquinone at 1000 mV/s scan rate).

The results show that the electrode reaction of hydroquinone is quasi-reversible on the carbon electrode. The reaction was chemically reversible but the kinetics were not. Despite the non-ideal behavior of Reaction 2, the anodic peak height in CV was linearly correlated to the concentration of reactant in the range from 0.05 to 10 mM when the scan rate was 1000 mV s$^{-1}$, see FIGS. 4 and 5.

Figure 6:
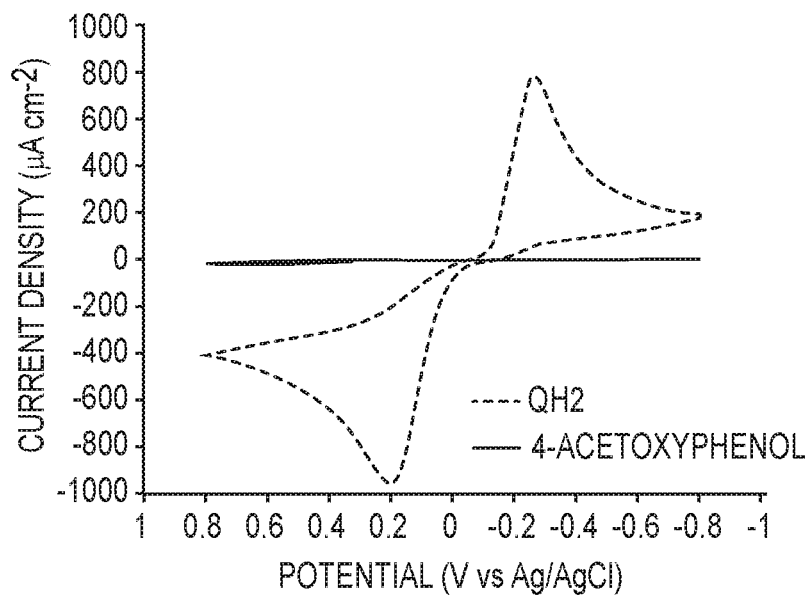
FIG. 6 shows cyclic voltammograms of hydroquinone and 4-acetoxyphenol.

FIG. 6 shows cyclic voltammograms of hydroquinone and 4-acetoxyphenol.

The electrochemistry of quinone has been extensively studied and employed in many applications. The interconversion between 1,4-benzoquinone (Q) and the corresponding hydroquinone (QH$_2$) is complex as the reaction involves two electron transfer reactions and two protonation steps. The mechanism is dependent on pH, working potential, and the reaction medium. A nine-membered square scheme was used to analyze the pathways for the intermediate interconversion via electron transfer and protonation. In phosphate buffer at pH 7.2, Reaction 2 gave two widely separated peaks (ΔE=334 mV) in cyclic voltammetry with a glassy carbon electrode. The pathway for Reaction 2 was postulated to involve a HeHe mechanism, although these four reactions could involve concerted steps.

The proposed AchE substrate 4-acetoxyphenol did not undergo any redox reactions in CV. This is consistent to an earlier report, indicating the oxidation took place at 1.1 V (vs Ag/AgCl) with a glassy carbon electrode. The large difference in oxidation potentials between the substrate and product is highly desirable for selective determination of QH$_2$. It is feasible to develop an amperometric method based on Reaction 2 in a way similar to the reaction with 4-aminophenyl acetate as the substrate. The oxidation of 4-aminophenol is more complicated as it involves two electron transfer, and two protonation reactions to give p-iminoquinone as the intermediate; which is subsequently hydrolyzed to give Q as the final product. 4-Aminophenol acetate was oxidized when the potential was above 0.4 V (with a sodium chloride saturated calomel electrode) in 0.1 M phosphate at pH 7.9. It also gave significant background in CV in 0.1 M phosphate, pH 7.5. It was not widely adopted for AchE sensor because it can undergo spontaneous oxidation. 4-Acetoxyphenol offers the advantages of a simpler reaction mechanism, a cleaner background, and improved stability.

Figure 7:
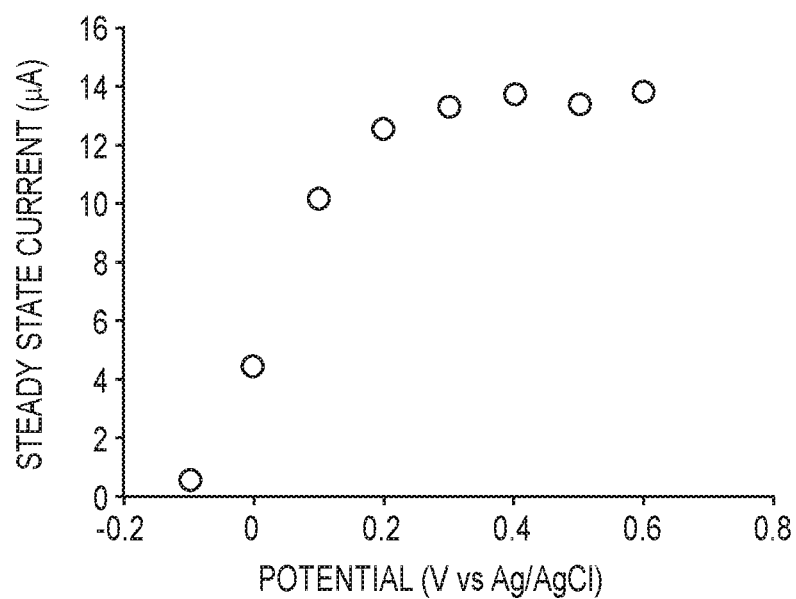
FIG. 7 illustrates a voltammogram of hydroquinone (2 mM in 0.1 phosphate, pH 7.0).

Voltammetry study with 2 mM QH$_2$ shows that the oxidation started from 0 V. The steady state current increased linearly as the potential increased to 0.2 V, then leveled off at higher potential, see FIG. 7. Therefore, the working potential was set at 0.35 V for maximum response. Amperometric assay with working potential at 0.35 V gave a linear correlation between steady state current and [QH$_2$] in the range between 0.05 to 10 mM. Regression analysis showed that the sensitivity was 8.76 μA mM$^{-1}$. For 4-acetoxyphenol, there was also a low yet appreciable current with a sensitivity of 0.150 μA mM$^{-1}$. Therefore, the sensitivity for the product was 57 folds higher than that for the substrate. Based on the result from CV study, 4-acetoxyphenol was unlikely to be oxidized at 0.35 V. However, it might undergo spontaneous hydrolysis to give $QH_2$, which was oxidized to give the background current. Another plausible cause of the background current is from impurity, as the substrate was only 96% pure. These concerns are addressable by a study with purified 4-acetoxyphenol.

Figure 8:
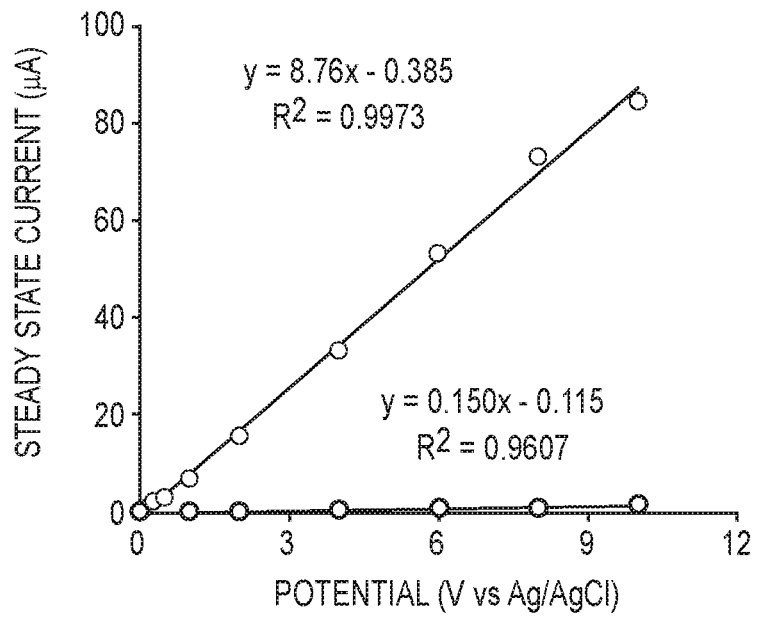
FIG. 8 illustrates standard curves for amperometric assay at 0.35 V for hydroquinone and 4-acetoxyphenol.

FIG. 8 illustrates standard curves for amperometric assay at 0.35 V for $QH_2$ (upper line) and 4-acetoxyphenol (lower line).

Immobilization of AchE and Hydrolysis of 4-Acetoxyphenol

The formation of $QH_2$ by HPLC (data not shown) was observed when 4-acetoxyphenol was incubated with AchE in 0.1 M phosphate buffer, pH 7. The rate of $QH_2$ formation depended on the amount of AchE and incubation time. Since no product was found in the control, it was concluded that AchE could catalyze Reaction 1.

A two-stage protocol was utilized in which the protein solution was deposited and air-dried on the working electrode, followed by applying GA solution to crosslink the proteins. Immobilizing AchE on the working electrode significantly increased the steady state current in the solution of 4-acetoxyphenol, and the current is dependent on the load of AchE. Therefore, the transduction based on the hydrolysis of 4-acetoxyphenol is feasible for AchE activity assay.

In the initial optimization of AchE immobilization, the variables included the amount of AchE and BSA, the buffer, and the concentration of GA. The objective was to maximize the steady state current. The assay was carried out in 0.1 M phosphate, pH 7.0 because the reverse reaction in As(III) inhibition (Equation 1) was slower in phosphate buffer. The substrate concentration was 20 mM.

For the first step, the impact of AchE was investigated in the range of 0.5-10 µg, BSA in the range of 0-30 µg in 0.1 M phosphate with pH between 6.5-7.5, see Table 3. In the evaluations summarized in Table 3, the concentration of AchE was fixed at 5.3 µg/electrode.

TABLE 3

Impact of Crosslinking Factors on the Steady State Current and Inhibition by 1 mM As(III)

| Electrode | pH | BSA (µg) | GA (%) | Steady State Current (µA) | Inhibition (%) |
|---|---|---|---|---|---|
| 1 | 7.5 | 30 | 0.015 | 82.2 | 59.1 |
| 2 | 7 | 20 | 0.015 | 87.5 | 65.7 |
| 3 | 6.5 | 30 | 0.005 | 77.4 | 69.6 |
| 4 | 7 | 20 | 0.01 | 79.2 | 61.7 |
| 5 | 7 | 10 | 0.01 | 88.6 | 63.0 |
| 6 | 6.5 | 20 | 0.01 | 90.9 | 68.0 |
| 7 | 7.5 | 20 | 0.01 | 81.2 | 63.4 |
| 8 | 6.5 | 30 | 0.015 | 86.2 | 65.1 |
| 9 | 7.5 | 10 | 0.015 | 65.9 | 67.1 |
| 10 | 6.5 | 10 | 0.005 | 93.3 | 71.7 |
| 11 | 7 | 30 | 0.01 | 105.3 | 65.8 |
| 12* | 7.5 | 30 | 0.005 | 36.3 | 74.7 |
| 13 | 7.5 | 10 | 0.005 | 106.1 | 70.7 |
| 14 | 7 | 20 | 0.01 | 88.0 | 66.9 |
| 15 | 6.5 | 10 | 0.015 | 70.0 | 66.0 |
| 16 | 7 | 20 | 0.005 | 95.2 | 69.3 |

For the crosslinking step, the GA concentration was evaluated from 0.001% to 0.015%. Other than the pH value of phosphate buffer, all factors had strong impact on the activity of AchE electrode. The yield of the current ranged from about 7-50 µA µg$^{-1}$ of AchE in the scope of conditions. The concentration of GA was the most significant factor. For crosslinking of 5.3 µg AchE with 10 µg of BSA, increasing GA from 0.005 to 0.015% caused current decrease from 99.7 µA to 68 µA. BSA stabilized AchE in the immobilization. When GA was set at 0.01%, increasing BSA from 10 to 30 µg caused current increase from 88.6 to 105.3 µA. In general, the concentration of GA should be adjusted based on the total protein, see Table 3.

Higher concentration of GA also reduced the sensitivity to As(III) inhibition. For crosslinking of 5.3 µg AchE with 20 µg of BSA, increasing GA from 0.005 to 0.015% caused a reduction of maximum inhibition (measured with 1 mM sodium arsenite) from 69.3% to 65.7%. A similar trend was observed for other combinations of crosslinking condition, see Table 3.

Figure 9:
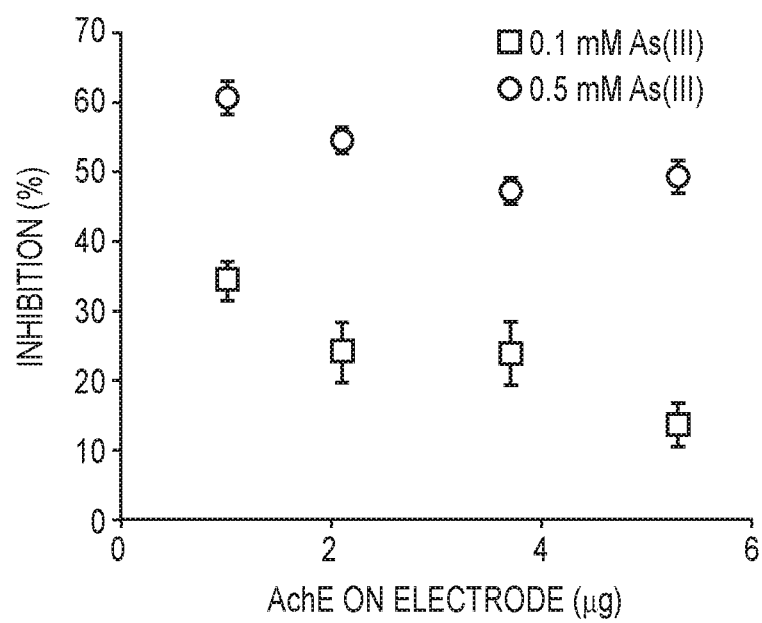
FIG. 9 illustrates inhibition as the amount of immobilized AchE varies.

Importantly, the sensitivity to the inhibition had an inverse correlation with the amount of AchE in the range from 1 to 5 µg, see FIG. 9. FIG. 9 illustrates dependence of inhibition on the amount of immobilized AchE. The electrode was prepared by crosslinking 5 µg (circle) or 1 µg (square) of AchE with 10 µg of BSA by 10 µl of 0.005% GA (n=3). This trend was observed at both 0.1 mM and 0.5 mM of As(III). To finalize the optimization, the amount of AchE to 0.5 µg was further reduced and the amount of BSA was adjusted to 8 µg. The protein mixture was immobilized by crosslinking with 10 µl of 0.0021% GA. The electrodes fabricated under this condition was more sensitive. The inhibition was about 55% with 100 µM As(III).

Figure 10:
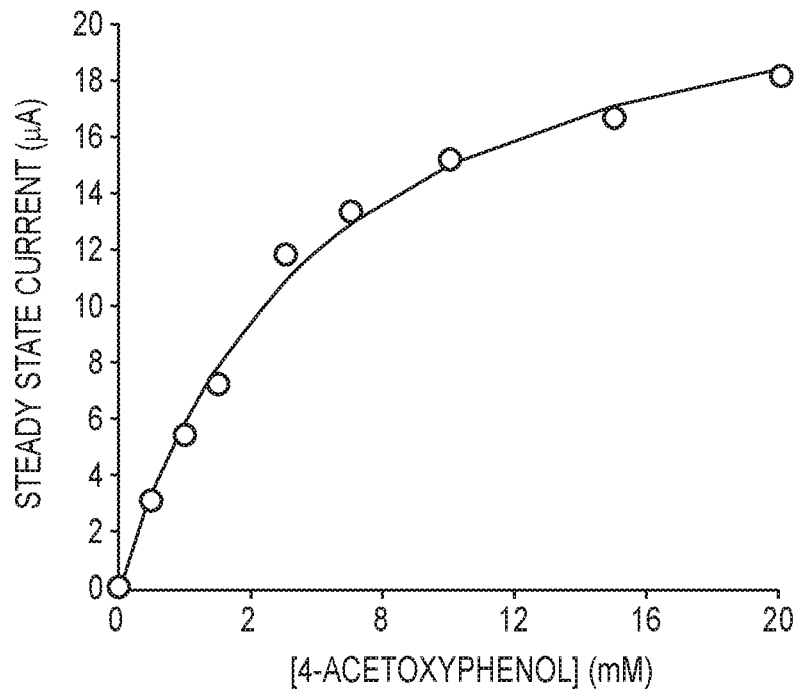
FIG. 10 illustrates steady state current as concentration of 4-acetoxyphenol varies.

There was a clear dependence of steady state current on the substrate concentration with the AchE electrode, see FIG. 10. FIG. 10 illustrates dependence of steady state current on substrate concentration. Fitting the data to Michaelis-Menten equation gave a model with $R^2$=0.9931, indicating the immobilized AchE exhibited similar kinetics to that in the free form, in which the reaction was diffusion controlled. The $V_{max}$ was 24.2±1.1 µA, corresponding to a current density of 121+5.25 µA cm$^{-2}$. The KM was 5.92±0.65 mM. When substrate concentration was set at 20 mM, the reaction rate should be 77% of the $V_{max}$.

Figure 11:
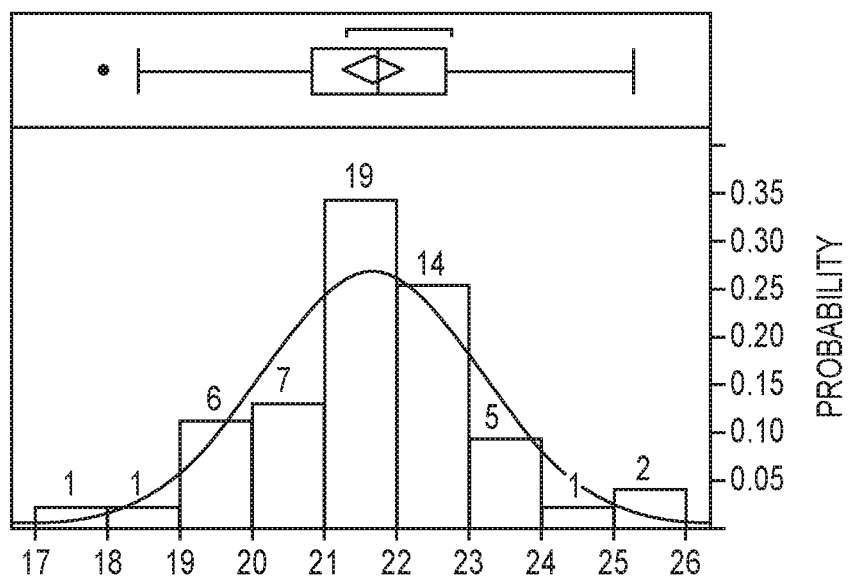
FIG. 11 illustrates distribution of initial steady state current ($A_o$) of AchE electrodes.

The immobilization protocol was efficient for the preparation of AchE electrodes. In an evaluation with 56 electrodes, the initial steady state current ($A_0$) ranged from 17.9-26.8 µA. The $A_0$ distribution appears to be random (Shapiro-Wilk test W=0.9793, Prob<W 0.4455), see FIG. 11. FIG. 11 illustrates the distribution of $A_0$ of the AchE electrodes made by glutaraldehyde immobilization. The average $A_0$ was 21.7±1.5 µA. One can routinely prepare 100 electrodes per day. It would be feasible to produce enough sensors to support field study at this productivity.

Figure 12:
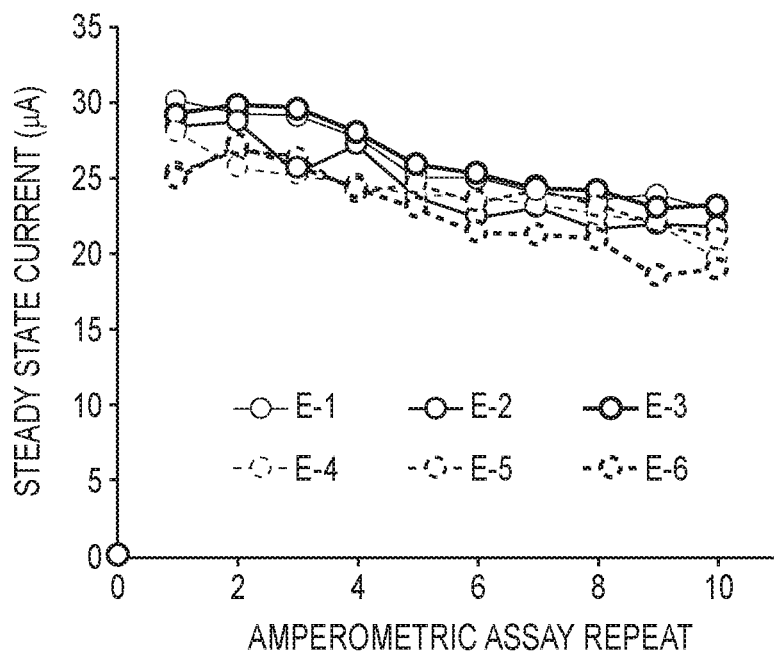
FIG. 12 illustrates change of steady state current of six (6) AchE electrodes in repeated uses.

In repeated use, these electrodes showed limited operational stability. The electrodes all underwent activity loss in 10 repeated uses. In each successive use, the steady state current was reduced by about 2-4%, see FIG. 12. If re-use is needed, all the measurements would need to have the same repeats. Since the current material cost is less than $3 per electrode, it is preferable to use these electrodes as one-use, disposable sensors.

Inhibition of Immobilized AchE and Measurement Protocol

It was previously shown that Tris and high pH facilitated the binding of As(III) to free AchE, therefore the inhibition study was carried out by incubating the electrode in arsenite solution in 0.1 M Tris-HCl, pH 8.0. The concentration of As(III) was 5, 20, and 100 µM, respectively; and samples were taken over the course of one hour.

Figure 13:
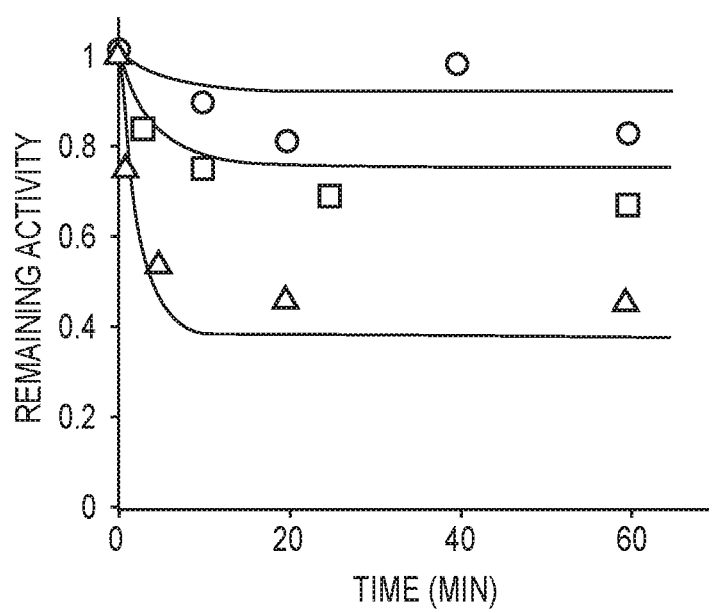
FIG. 13 illustrates inhibition of immobilized achE by arsenite.

The rate and extent of inhibition was found to be similar to the case with free AchE, which was dependent on both time and As(III) concentration, see FIG. 13. FIG. 13 illustrates inhibition of immobilized AchE by Arsenite (circles, 5 µM, squares 20 µM, triangles 100 µM). Fitting the data to a model based on the reversible pseudo-first order mechanism (Equation 1) gave a $k_1$ of $2.84 \times 10^3$ $M^{-1}$ $min^{-1}$, and a of $1.75 \times 10^{-1}$ $M^{-1}$. Apparently, the association and dissociation for immobilized AchE were both faster than those for free AchE. The regression coefficient $R^2$ was 0.7475 for this fitting, suggesting that the kinetics might not be fully represented by the model. Nevertheless, it was clear that the protocol previously reported based on a steady state mechanism with rapid binding was unsuitable as the equilibrium was not reached instantaneously. In addition, the mechanism showed that dissociation was still slow enough that the reaction could be treated as being irreversible in protocol development. Since the $K_i$ was $6.16 \times 10^{-5}$ M, the lower detection limit should be in low µM concentrations.

Based on the kinetic feature, the evaluation protocol involved a one-hour incubation of the electrode in arsenite solution in 0.1 M Tris-HCl, pH 8.0 followed by residual activity ($i_r$) determination. The inhibition was calculated by Equation 2. The inhibition increased rapidly in the concentration range of 2-20 µM of As(III), then much slower as the concentrations were between 20-500 µM, see FIG. 14A. Over the wide dynamic range, the dependence of inhibition on [As(III)] could be represented with a logarithm relationship. $I_{Max}$ was typically 70-75%, much higher than those reported earlier.

Figure 14A:
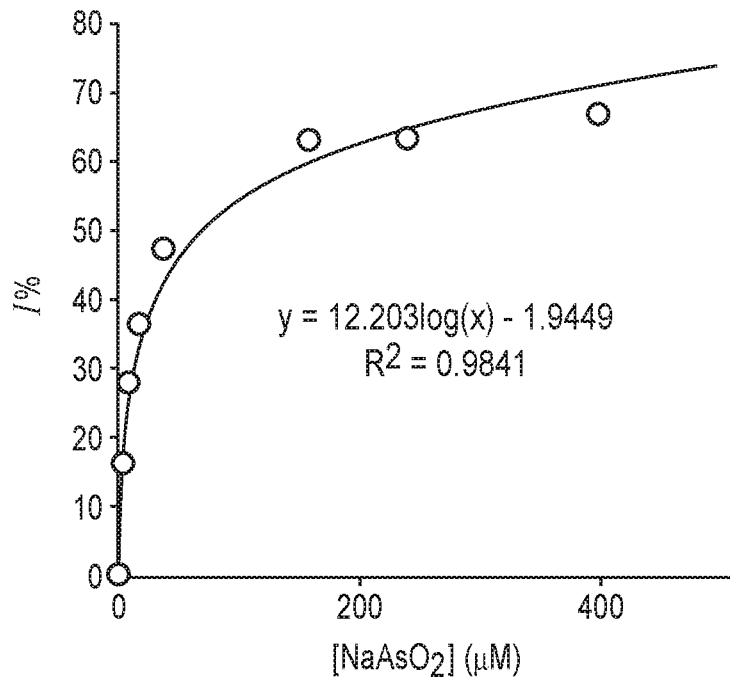
FIGS. 14A and 14B illustrate correlation between I % and concentration of As(III) in Tris-HCl buffer.
Figure 14B:
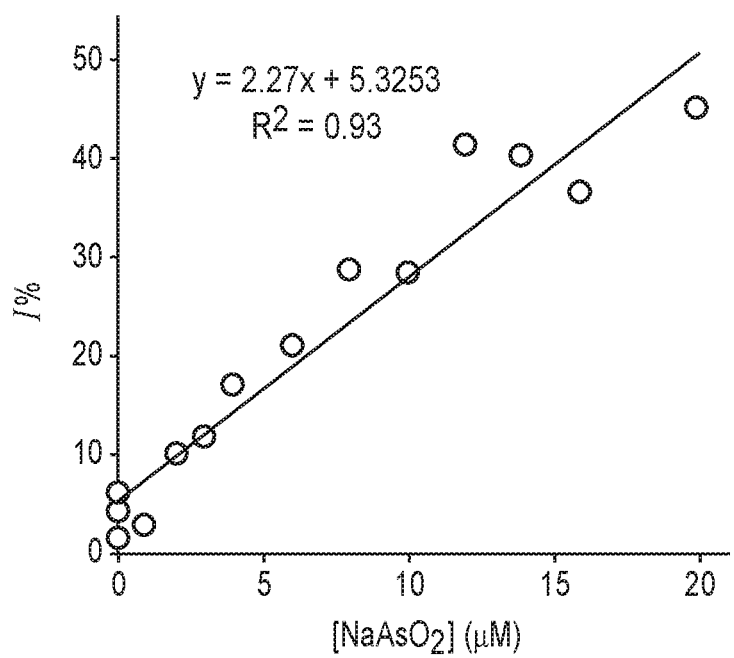

FIGS. 14A and 14B illustrate the correlation between I % and [As(III)] in Tris-HCl buffer.

A focused evaluation at lower range of As(III) revealed detailed characteristics of the sensor, see FIG. 14B. Corresponding to 1 to 20 µM As(III), the inhibition increased from 2.7 to 44.9%. Least square regression gave a straight line with a $R^2$ of 0.93. The line had an intercept (I %) of 5.3±1.68, and a slope (I % µM$^{-1}$) of 2.27±0.18. Therefore, the limit of detection (LOD) was 3σ+intercept=10.3% of uncorrected inhibition, corresponding to the concentration of As(III) at 2.2 µM. This result was consistent with kinetic data. The estimated inhibition at 20 µM was 50.7±5.7%.

The current AchE biosensor is useful for field testing of samples with [As(III)]>2 µM (150 ppb). To expand its application, its sensitivity and precision could be increased through precise immobilization and bioreceptor improvement.

Speciation of As(III) and Correlation to ICP-AES Measurement

The AchE sensor was evaluated for speciation with mixtures of 5 µM $Na_2HAsO_4 \cdot 7H_2O$ with 0-20 µM of $NaAsO_2$ in 0.1 M Tris-HCl, pH 8.0. The concentration of As (III) was determined by the AchE sensor, while the concentration of total arsenic was validated by ICP-AES.

The recovery of As (III) based on AchE-sensor ranged from 95-170%, see Table 4. At concentrations of 2 and 4 µM, the test results were 60-70% higher than the real value. There are also large standard deviations associated to the results. This is probably caused largely by random error; because at low [As(III)] the equilibrium takes longer to reach and more sensitive to random interference. In addition, systematic error caused by linear fit may also be significant. The accuracy of determination could be improved by spiking with known amount of As(III) to 8 µM-20 µM, where the recoveries are between 95-109%.

TABLE 4

Speciation Composition and Results by ICP-AES and AchE-Sensor

| Test | As(V) (µM) | As(III) (µM) | ICP-AES (µM) | Total As Recovery (%) | AchE-Sensor (µM, n = 5) | Average As(III) Recovery (%) |
|---|---|---|---|---|---|---|
| 1 | 5.0 | 0.0 | 5.20 | 104 | −3.70 ± 3.44 | |
| 2 | 5.0 | 2.0 | 7.19 | 102 | 3.40 ± 2.05 | 170 |
| 3 | 5.0 | 4.0 | 9.21 | 101 | 6.46 ± 2.30 | 161 |
| 4 | 5.0 | 8.0 | 13.17 | 101 | 8.73 ± 1.01 | 109 |
| 5 | 5.0 | 14.0 | 19.33 | 101 | 14.11 ± 1.15 | 100 |
| 6 | 5.0 | 20.0 | 25.32 | 101 | 19.00 + 1.15 | 95 |

Figure 15:
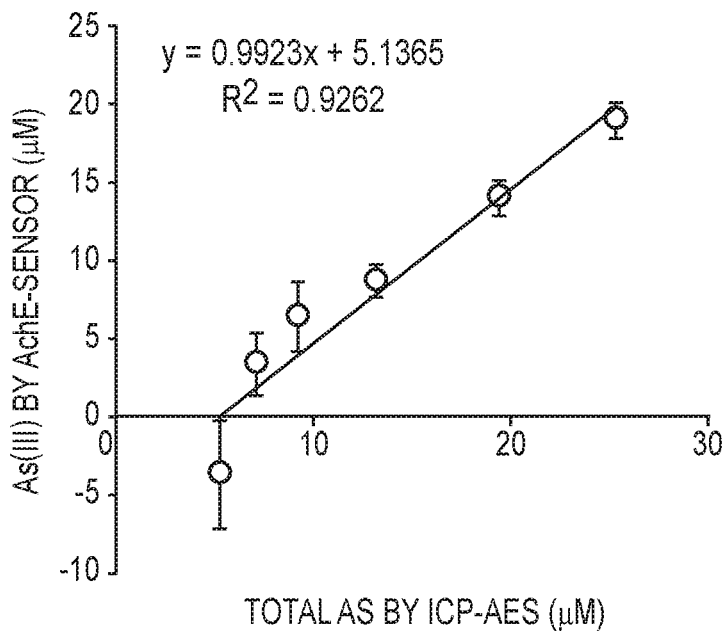
FIG. 15 is a comparison of total arsenic determined by ICP-AES and As(III) determined by AchE sensor.

The results from the AchE sensor and ICP-AES are highly correlated as shown by the cross-comparison, see FIG. 15. FIG. 15 illustrates comparison of total As determined by ICP-AES and As(III) determined by AchE-sensor. Regression analysis gives a line with a slope of 0.992±0.140, an intercept of −5.13±2.1 (µM) and $R^2$=0.9262. Based on the equation, the x-intercept is 5.17 µM, confirming that the sensor is not sensitive to As(V).

Determination of As(III) in Simulated Groundwater

The impact of groundwater on the AchE sensor was evaluated using synthetic groundwater. The composition was created based on the water chemistry data collected in the Shepley's Hill Landfill Superfund Site at Fort Devens, Mass. The concentration of a cation was the median of its concentrations in 41-43 samples. The concentration of an anion was the median of its concentrations in 36-43 samples, see Table 5.

TABLE 5

The Composition of a Synthetic Groundwater Based on the Water Chemistry in Shepley's Hill Landfill in Fort Devens, MA

| Salt | [cation] (µM) | $CO_3^{2-}$ (µM) | $Cl^-$ (µM) | $SO_4^{2-}$ (µM) | Silicate (µM) | $PO_4^{3-}$ (µM) |
|---|---|---|---|---|---|---|
| $FeCl_2$ | 612 | | 612 | | | |
| $MnCl_2$ | 83 | | 83 | | | |
| $CaCO_3$ | 1105 | 1105 | | | | |
| $K_2CO_3$ | 213 | 106 | | | | |
| $MgSO_4$ | 256 | | | 256 | | |
| $NaHCO_3$ | 847 | 847 | | | | |
| $(NH_4)_2CO_3$ | 143 | 72 | | | | |
| $Na_2SiO_3$ | 400 | | | | 400 | |
| $Na_2HPO_4$ | 100 | | | | | 100 |
| Total | | 2130 | 695 | | | |

The groundwater was largely anoxic but not sulfidic, with a mean oxidation-reduction potential at −99.5±6.77 mV. Nitrogen existed as ammonia. All iron was Fe(II). The Fe(II) in nitrogen sparged synthetic groundwater was stable for less than 6 hours, therefore the groundwater was prepared freshly. To promote the AchE inhibition by As(III), Tris salt was added to the groundwater sample at a concentration of 0.1 M, pH 8.

Figure 16:
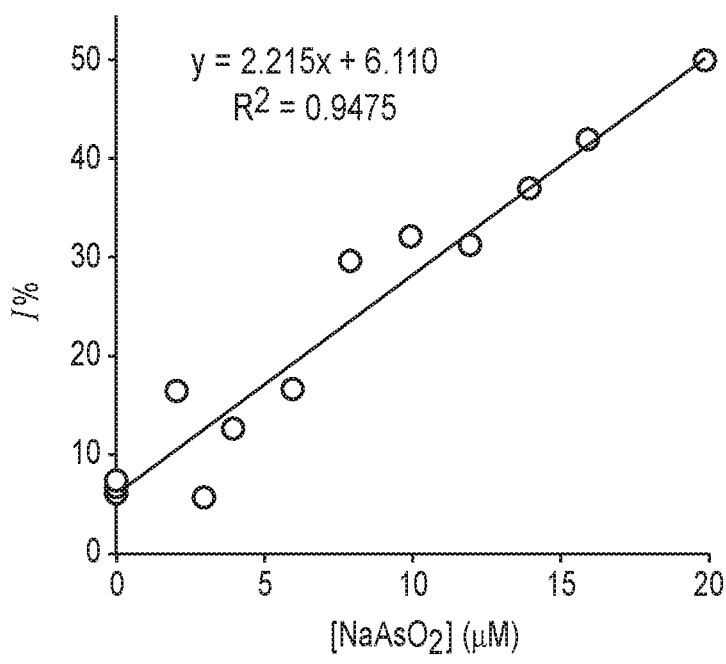
FIG. 16 illustrates correlation between I % and concentration of As(III) in synthetic groundwater.

FIG. 16 illustrates the correlation between I % and [As (III)] in synthetic groundwater.

The standard curve with groundwater is similar to that with Tris-HCl. Between 0-20 µM, the inhibition was 6-49%. The detection limit is 8.6%, corresponding to 1.1 µM (82.5 µg L$^{-1}$). The ratio of the regression slopes is 97.6%, suggesting a nearly full recovery in the groundwater matrix.

Storage Stability of the AchE Electrode

A 6-day activity loss of AchE electrodes was evaluated in buffers including phosphate or Tris-HCl with pH from 6 to 8, at temperatures from 4-25° C. It was found the electrodes had essentially no activity loss in 0.1 M Tris-HCl, pH 7.0 under ambient temperature (22±2° C.). Prolonged evaluation with AchE electrodes from the same batch showed that they were stable over 150 days, see FIG. 17.

Figure 17:
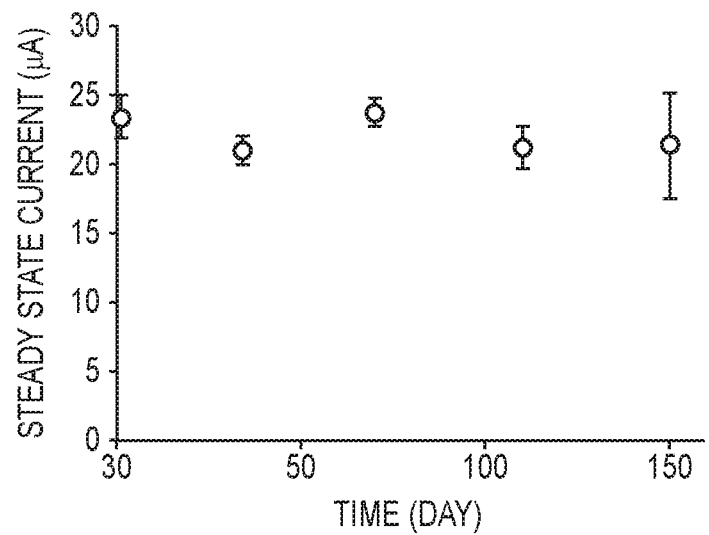
FIG. 17 illustrates storage stability of AchE electrodes in 0.1M Tris-HCl, pH 7.0 at 20-24° C.

FIG. 17 shows storage stability of the AchE electrodes in 0.1 M Tris-HCl, pH 7.0 at 20-24° C. (n=5 for each time point).

Arsenic pollution from anthropogenic sources poses great environmental risk because As concentration is usually very high (>ppm level) at the origin. Groundwater contamination is the most important pathway for arsenic transportation from anthropogenic sources. The migration and sequestration can be highly complicated because the migration depends on the geochemistry, hydrology, and climate in local area. A disposable field sensor for speciation is highly desirable to characterize the spatial and temporal variations of As(III). The speciation information would be useful to better characterize the arsenic plume in groundwater, differentiate the sources of arsenic in groundwater, understand the stability of arsenic associated with the sediment, and evaluate the risk of surface water contamination from groundwater discharge.

CONCLUSION

To address the unmet need for As speciation in field, a disposable AchE sensor has been developed based on practical needs. A novel reaction sequence for signal transduction was employed to simplify sensor design. The amperometric assay was used to optimize sensor fabrication, evaluate the mechanism for AchE inhibition by As(III), and characterize sensor performance. This sensor has a linear range of 0-20 µM, with LOD of 1-2 µM As (III). It can determine As(III) in the mixture with As(V) as validated by ICP-AES. The sensor has been manually fabricated with a throughput of 100 day$^{-1}$ person$^{-1}$. It is stable for 150 days at room temperature. Therefore, this lab-made sensor can be used to characterize water pollution in anthropogenic sites.

Figure 18:
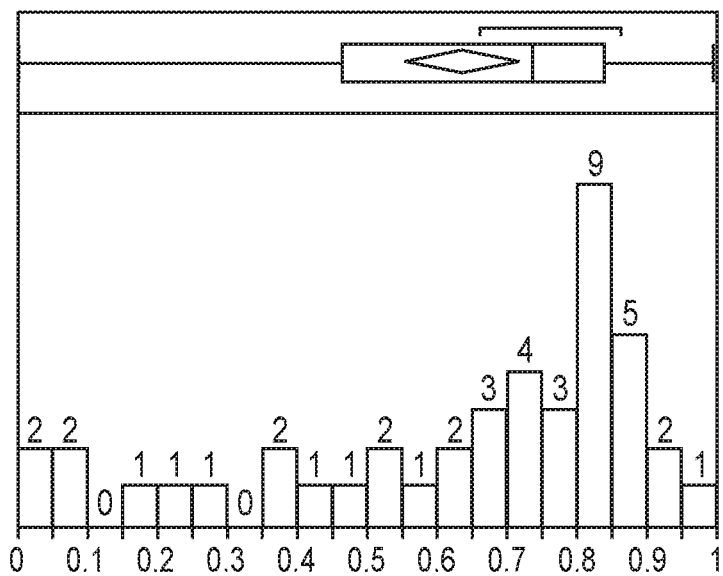
FIG. 18 illustrates distribution of total arsenic in various groundwater samples.

An example of the potential application of the biosensor would be for the characterization of groundwater pollution in Shepley's Hill Landfill Superfund Site. The overall As(III) recovery from simulated groundwater matrix is 97.6% in the range of 0-20 µM (1500 µg L$^{-1}$). The sensitivity is adequate to locate the hot spots of As(III) along with their spatial and temporal scales. In one survey, the concentrations of total As ranged from 177-995 µg L$^{-1}$ (2.4-13.3 µM) in 39 out of 43 samples, see FIG. 18. FIG. 18 illustrates distribution of total arsenic (mg L$^{-1}$) in 43 groundwater samples from Shepley's Hill Landfill Superfund Site at Fort Devens, Mass. According to water chemistry and prior surveys, the As was expected to be mostly arsenite. Combined with geographic system information, the sensor can be used to generate maps of As(III) plume with 150 µg L$^{-1}$ boundary concentration.

Many other benefits will no doubt become apparent from future application and development of this technology.

All patents, applications, standards, and articles noted herein are hereby incorporated by reference in their entirety.

The present subject matter includes all operable combinations of features and aspects described herein. Thus, for example if one feature is described in association with an embodiment and another feature is described in association with another embodiment, it will be understood that the present subject matter includes embodiments having a combination of these features.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A biosensor for analyzing a sample for pollutant agents in water, the biosensor comprising:
   a substrate;
   an electrode; and
   at least one enzyme immobilized on the electrode;
   wherein the substrate includes 4-acetoxyphenol.

2. The biosensor of claim 1, wherein the pollutant agents include As(III).

3. The biosensor of claim 1 further comprising:
   at least one electrode.

4. The biosensor of claim 1 wherein the enzyme is acetylcholinesterase (AchE).

5. The biosensor of claim 1 wherein the enzyme is selected from the group consisting of AchE, Lipase AY-S, Lipase AS, Lipase PS SD, Lipase G, Lipase AK, Lipase R, Lipase DF, Lipolase 100 L, Lipex 100 L, NovoCor AD L (Lipase A), Lipozyme CALB L, Palatase 20000 L, Alcalase 2.5 Type DX, Savinase 16 L, Umamizyme-K, Peptidase R, Protease M Amano SD, Protease P Amano 6SD, Protease A Amano2SD, L-Acylase H Amano, D-amino acylase, and combinations thereof.

6. The biosensor of claim 1 wherein the substrate also includes a monoester of a benzene diol.

7. The biosensor of claim 6 wherein the monoester of a benzene diol is selected from the group consisting of a monoester of hydroquinone, a monoester of resourcinol, a monoester of catechol, and combinations thereof.

8. The biosensor of claim 3 wherein the substrate is remote from the at least one enzyme and the at least one electrode.

9. A biosensor for analyzing a sample, the biosensor comprising:
   a substrate including 4-acetoxyphenol, the substrate defining a first face and a second face;
   a working electrode disposed on the first face of the substrate;
   a region including at least one enzyme disposed on the working electrode.

10. The biosensor of claim 9 wherein the enzyme is acetylcholinesterase (AchE).

11. The biosensor of claim 9 further comprising:
    a reference electrode disposed on the substrate;
    a counter electrode disposed on the substrate.

12. The biosensor of claim 9 wherein the enzyme is selected from the group consisting of AchE, Lipase AY-S, Lipase AS, Lipase PS SD, Lipase G, Lipase AK, Lipase R, Lipase DF, Lipolase 100 L, Lipex 100 L, NovoCor AD L (Lipase A), Lipozyme CALB L, Palatase 20000 L, Alcalase 2.5 Type DX, Savinase 16 L, Umamizyme-K, Peptidase R, Protease M Amano SD, Protease P Amano 6SD, Protease A Amano2SD, L-Acylase H Amano, D-amino acylase, and combinations thereof.

13. The biosensor of claim 9 wherein the substrate also includes a monoester of a benzene diol.

14. The biosensor of claim 13 wherein the monoester of a benzene diol is selected from the group consisting of a monoester of hydroquinone, a monoester of resourcinol, a monoester of catechol, and combinations thereof.

15. A method for detecting presence of a pollutant agent, the method comprising:
providing a biosensor including a substrate having 4-acetoxyphenol, a working electrode disposed on the substrate, and a region including at least one enzyme disposed on the working electrode;
exposing the biosensor to an aqueous sample;
monitoring electrical activity at the working electrode.

16. The method of claim 15 wherein the enzyme is acetylcholinesterase (AchE).

17. The method of claim 15 wherein the enzyme is selected from the group consisting of AchE, Lipase AY-S, Lipase AS, Lipase PS SD, Lipase G, Lipase AK, Lipase R, Lipase DF, Lipolase 100 L, Lipex 100 L, NovoCor AD L (Lipase A), Lipozyme CALB L, Palatase 20000 L, Alcalase 2.5 Type DX, Savinase 16 L, Umamizyme-K, Peptidase R, Protease M Amano SD, Protease P Amano 6SD, Protease A Amano2SD, L-Acylase H Amano, D-amino acylase, and combinations thereof.

* * * * *